United States Patent [19]

Zylstra

[11] Patent Number: Plant 6,266

[45] Date of Patent: Aug. 30, 1988

[54] *OLEA EUROPAEA* CV. MONTRA

[75] Inventor: Dick Zylstra, Goleta, Calif.

[73] Assignee: Monrovia Nursery Company, Azusa, Calif.

[21] Appl. No.: 887,336

[22] Filed: Jul. 21, 1986

[51] Int. Cl.[4] ..... A01H 5/03
[52] U.S. Cl. ..... Plt./33
[58] Field of Search ..... Plt./33

*Primary Examiner*—Robert E. Bagwill

[57] ABSTRACT

A new and distinct selection of *Olea europaea* L. (popularly known as Common Olive) which shall be referred to hereinafter as *Olea europaea* cultivar Montra. *Olea europaea* cultivar Montra differs distinctively from other olives by a unique combination of a dwarf shrub habit, a rapid grower when young and a dense compact growth habit.

1 Drawing Sheet

DISCOVERY

This invention relates to a new and distinct selection of *Olea europaea,* a member of the Oleaceae or olive family. *Olea europaea* cv. Montra was discovered by me in a group of *Olea europaea* at West Covina Wholesale Nursery, 938 South California Avenue, West Covina, Calif. in 1973. The plant to date is known only to exist within the boundaries of West Covina Wholesale Nursery and Monrovia Nursery Company, 18331 East Foothill Boulevard, Azusa, Calif. and has not been offered for sale or described in any publication.

REPRODUCTION

My new selection has been strictly asexually reproduced by cuttings at West Covina Wholesale Nursery and Monrovia Nursery Company. The distinct phenotypic characteristics of this new selection that set this plant apart from other olive plants could be lost genetically through sexual reproduction. Therefore, sexual reproduction is prohibited and propagation is restricted to asexual reproduction by cuttings. Seed progeny from the new selection has not been observed.

BRIEF DESCRIPTION OF THE DRAWINGS

The accompanying illustrations show a typical specimen of the plant according to this invention and are depicted in color as nearly true as possible.

FIG. 1 depicts a closeup of my new selection exhibiting the dense bushy habit so unusual for an olive which generally forms a large tree. Foliage size is similar in shape to an average olive though the dwarf shrub-like habit makes this a unique selection.

This comparison shot of an olive tree with my dense olive bush is shown in FIG. 2.

DESCRIPTION

Below is a detailed description of the new *Olae europaea* cv. Montra, the color terminology is from The British Horticultural Color Charts.

Overall size and habit: Evergreen, dense, after 10 years plant is approximately 3½ feet in height and width.

Foliage:

*Shape.*—Elliptic.
*Base.*—Cuneate.
*Tip.*—Small mucronate tip.
*Margins.*—Entire.
*Width.*—0.8 cm–1.5 cm.
*Length.*—2.2 cm–5.7 cm.
*Arrangement.*—Opposite and alternate.
*Petiole.*—2 mm to 4 mm.
*Color.*—Upper leaf surface: Spinach Green 0960. Lower leaf surface: Silvery.

Flower and fruit: Flowers have not been observed during the 10 years this plant has been under observation. Therefore, no fruit has been produced.

I claim:

1. A new and distinct selection of *Olea europaea* as substantially shown and described herein, that is characterized particularly as a novelty by the unique combination of a dwarf shrub habit, a rapid grower when young and a dense compact growth habit.

* * * * *

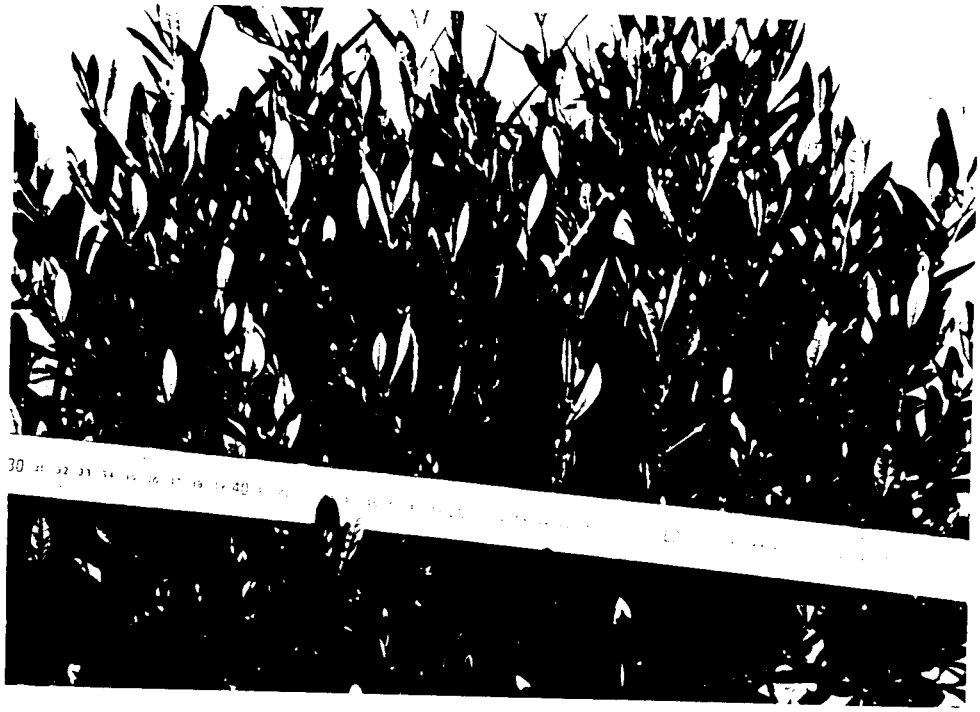
FIG. 1 SELECTION
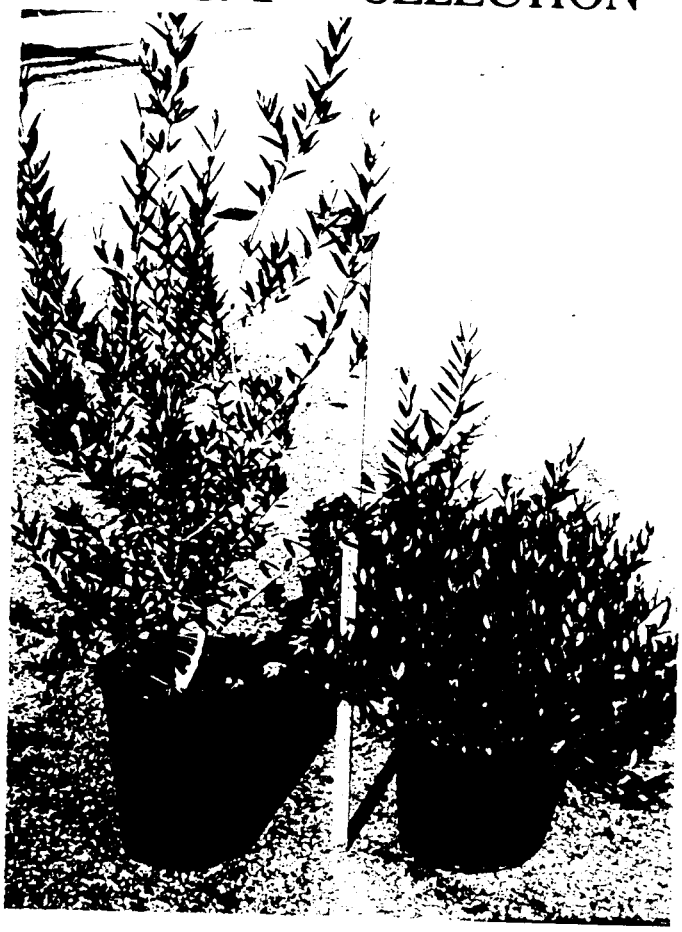
FIG. 2 PRIOR ART & SELECTION